US006998268B2

(12) United States Patent
Terada et al.

(10) Patent No.: US 6,998,268 B2
(45) Date of Patent: Feb. 14, 2006

(54) GENE PREPARATIONS

(75) Inventors: Masaaki Terada, Tokyo (JP); Takahiro Ochiya, Tokyo (JP); Teruo Miyata, Tokyo (JP); Hiroshi Itoh, Tokyo (JP)

(73) Assignees: Dainippon Sumitomo Pharma Co. Ltd., Osaka (JP); Koken Co., Ltd., Tokyo-to (JP)

( * ) Notice: Subject to any disclaimer, the term of this patent is extended or adjusted under 35 U.S.C. 154(b) by 296 days.

(21) Appl. No.: 10/261,618

(22) Filed: Oct. 2, 2002

(65) Prior Publication Data

US 2003/0082161 A1 May 1, 2003

Related U.S. Application Data

(63) Continuation-in-part of application No. 08/981,552, filed as application No. PCT/JP96/01824 on Jul. 2, 1996, now abandoned.

(30) Foreign Application Priority Data

Jul. 3, 1995 (JP) .................................. 7-167744

(51) Int. Cl.
C12N 15/63 (2006.01)
C12N 15/00 (2006.01)
A61K 38/17 (2006.01)
C07H 21/02 (2006.01)
A01N 43/04 (2006.01)

(52) U.S. Cl. .................. 435/455; 435/320.1; 530/356; 536/23.1; 514/44

(58) Field of Classification Search ............. 435/320.1, 435/455; 530/350, 356; 536/23.1; 514/44
See application file for complete search history.

(56) References Cited

U.S. PATENT DOCUMENTS

| 4,774,091 A | | 9/1988 | Yamahira et al. ........... 424/426 |
| 4,849,141 A | | 7/1989 | Fujioka et al. .............. 764/207 |
| 4,941,874 A | | 7/1990 | Sandow et al. ............... 604/60 |
| 5,236,704 A | * | 8/1993 | Fujioka et al. ............. 424/85.1 |
| 5,453,270 A | | 9/1995 | Bills ......................... 424/93.7 |
| 5,552,309 A | | 9/1996 | March ........................ 435/456 |
| 5,672,301 A | * | 9/1997 | Orly et al. ................... 264/4.1 |
| 5,763,416 A | | 6/1998 | Bonadio et al. .............. 514/44 |

FOREIGN PATENT DOCUMENTS

| EP | 0139286 | 5/1985 |
| EP | 0412554 | 2/1991 |
| EP | 0586700 | 3/1994 |
| JP | 393716 | 4/1991 |
| WO | 9524929 | 9/1995 |
| WO | 9600295 | 1/1996 |

OTHER PUBLICATIONS

K. Ozawa, Hematology & Oncology, 29(3) : 155-163 (1994).
V.L. Truong, Proceed. Intern. Symp. Control. Rel. Bioact. Mater., 21:142-143 (1994).
V.L. Truong, Proceed. Intern. Symp. Control. Rel. Bioact. Mater., 22:466-467 (1995).
K.L. March, Human Gene Therapy, 6:41-53 (Jan. 1995).
J. Muhlhauser, Human Gene Therapy, 6:1457-1465 (Nov. 1995).
J. Fang, Proc. Natl. Acad. Sci.. USA, 93:5753-5758 (Jun. 1996).
Sorscher et al., Human Gene Therapy 5/10. p. 1259-1270 (1994).
R.J. Mumper et al., Pharmaceutical Research, 13(5) : 701-709 (1996).
E.G. Nabel et al., Cardiovascular Research, 28:445-455 (1994).
W.F. Anderson, Science, 256:808-813 (1992).
A.G.Y. Chang et al., Gastroenterology, 106:1076-1084 (1994).
B. Dodet, TIBTECH, 11: 182-189 (1993).
K. Kato et al., The Journal of Biological Chemistry, 266(6): 3361-3364 (1991).
J. J. Donnelly, Nature Medicine, 1(6) : 583-587 (1995).
K. F. Kozarsky et al., The Journal of Biological Chemistry, 269(18) : 13695-13702 (1994).
Y. Setoguchi et al., Am J. Respir. Cell Mol. Biol., 10:369-377 (1994).
K. Fujioka et al., Journal of Controlled Release, 33:307-315 (1995).
Zhu Xiaojun et al., "Basic Research of Gene Therapy on Cardiovascular Disease", Journal of Beijing Medical University, vol. 26, pp. 131-133.
Wang Jianmin et al., "Clinical Studies on Gene Therapy for Hemophilia B", Chinese Journal of Hematology, Jun. 1994, vol. 15, No. 6, pp. 282-285.

* cited by examiner

*Primary Examiner*—Shin-Lin Chen
(74) *Attorney, Agent, or Firm*—Birch, Stewart, Kolasch & Birch, LLP (57) ABSTRACT

The present invention relates to gene preparations comprising desired genes or vectors containing desired genes integrated there into and carriers for supporting the same. The carrier is preferably a soluble collagen such as atelocollagen and may further include an additive. The invention also encompasses methods for delivering genes to cells employing the gene preparation.

19 Claims, 4 Drawing Sheets

GENE PREPARATIONS

RELATED APPLICATIONS

The present application is a Continuation-In-Part of U.S. application Ser. No. 08/981,552, filed Feb. 4, 1998 now abandoned. U.S. application Ser. No. 08/981,552 is the national phase under 35 U.S.C. § 371 of the prior PCT International application no. PCT/JP96/01824, which has an international filing date of Jul. 2, 1996, which designated the United States of America. The entire contents of all of the above applications are hereby incorporated by reference.

FIELD OF THE INVENTION

The present invention relates to the field of medicine, especially gene therapy. Especially, the present invention relates to a preparation containing a gene. The preparation retains a gene vector or a gene stably, releases it gradually and maintains the therapeutic effect for a long time when administered into a living body. The preparation makes it possible to stop a treatment at favorable period.

BACKGROUND OF THE INVENTION

Gene therapy is an active area of research, and expectation for successful therapy is extremely high. In gene therapy approaches in which the gene per se is the medicine, the therapy for disease is conducted by transferring a gene of a designated enzyme, cytokine, and the like into cells of a patient. The introduced gene then produces the designated substance in the patient's body. This gene therapy can be divided to two types. The purpose of the first type is semipermanent expression of designated gene by integrating the gene into genome of a patient. The purpose of another type is transient expression of a gene without expectation of its integration into genome. In the latter type of gene therapy, a method using adenovirus and the like is often adopted as a method for transferring into the patient a gene encoding, for example, a cytokine which increases immuno-potency against cancer cells (Cardiovascular Research, 28, 445 (1994); Science, 256, 808 (1992); Gastroenterology, 106, 1076 (1994); TIBTECH, 11, 182 (1993); J. Biol. Chem., 266, 3361 (1991); Nature Medicine, 1, 583, (1995); and references cited therein).

In the case of using a virus vector, though the efficiency of gene transfer is generally high, repeated administrations are difficult due to immune responses (J. Biol. Chem., 269, 13695 (1994), Am. J. Respir. Cell Mol., 10, 369 (1994)).

A preparation using collagen for gradually releasing medicines containing organic compounds or a protein preparation is disclosed in J. Controlled Release 33, 307–315 (1995), etc. However, the disclosed and usual medicine (for example, protein drug, medicine chemically synthesized, etc.) is dissolved in approximately 1–2 days when retained in, for example, collagen gel.

In a method which is presently used in gene therapy and comprises administering a gene vector (a gene-inserted vector) or a gene directly, the gene vector or the gene contacts cells immediately after administration, and immediately after that gene transfer starts and is completed at once. Furthermore, the gene transduced into cells is diluted (that is, its copy number decreases) with cell division or is reduced by degradation in cells. Therefore, expression of the transferred gene can be maintained only for several weeks which is too short to practice sufficient treatment and this is a deficiency in the method. Accordingly, repeated administrations of a gene vector or a gene are necessary. Therefore, an object of the present invention is to overcome these defects and provide a preparation, which can release a gene vector or a gene gradually and can maintain the therapeutic effect for a long time.

Furthermore, a method enabling repeated administrations is expected, because those are difficult in gene therapy using a virus vector and the like. Accordingly, a second object of the present invention is to provide a gene preparation enabling repeated administrations in gene therapy using a virus vector and the like.

Furthermore, it is desirable that gene expression in the body can be stopped any time to ensure safety, because a gene is expressed for several weeks, which is longer than the term for a protein preparation. Accordingly, a third object of the present invention is to provide a gene preparation which can make it possible to quickly stop the gene transfer when termination of treatment is intended.

SUMMARY OF THE INVENTION

The present inventors have examined various preparations for gradually releasing a gene vector or a gene and have found that, when a preparation wherein a gene or a vector inserted with a gene is incorporated into a carrier made of a biocompatible material was administered into a living body; the gene was unexpectedly expressed for many months. The present inventors have also found that the preparation can be administered repeatedly into a living body and thus the present invention has been accomplished.

Therefore, the characteristic features of the present invention are as follows.

(1) A gene preparation comprising a gene, wherein said gene or a vector inserted with said gene is incorporated into a carrier made of a biocompatible material.

(2) The gene preparation according to (1), wherein said biocompatible material is selected from the group consisting of collagen, gelatin, fibrin, albumin, hyaluronic acid, heparin, chondroitin sulfate, chitin, chitosan, alginic acid, pectin, agarose, hydroxyapatite, polypropylene, polyethylene, polydimethylsiloxane, polymer or copolymer of glycolic acid, lactic acid or amino acid, and a mixture of at least two of these biocompatible materials.

(3) A gene preparation comprising a gene, wherein said gene or a vector inserted with said gene is incorporated into a carrier made of a biocompatible material containing collagen.

(4) A gene preparation comprising a gene, wherein said gene or a vector inserted with said gene is incorporated into a carrier made of collagen.

(5) The gene preparation according to (1), wherein the content of said biocompatible material in said gene preparation is 0.01–30 w/w % when administered into a living body.

(6) The gene preparation according to (1), which is in a form of a solution, suspension, water-containing gel, film, sponge, rod or sphere.

(7) The gene preparation according to (1), wherein said vector is selected from the group consisting of a virus vector, a liposome vector and a fusogenic liposome vector in which a virus and a liposome are fused.

(8) The gene preparation according to (1), wherein said vector is a virus vector.

(9) The gene preparation according to (1), wherein said vector is an adenovirus vector.

(10) A gene preparation comprising a gene, wherein said gene or a vector inserted with said gene is incorporated into

DETAILED DESCRIPTION OF THE INVENTION

The present invention will be described below in more detail.

"A vector for gene insertion" maybe any vector that can transfer a gene in to cells and includes, for example, a virus vector, a liposome vector, a fusogenic liposome vector in which a virus and a liposome are fused, or the like (Cardiovascular Research, 28, 445 (1994); Science, 256, 808 (1992); Gastroenterology, 106, 1076 (1994); TIBTECH, 11, 182 (1993); J. Biol. Chem., 266, 3361 (1991); Nature Medicine, 1, 583, (1995); and references cited therein).

A virus vector may be any vector that can be used as an ordinary vector in gene therapy and includes, for example, an adenovirus, an adeno-associated virus, a vaccinia virus, a retrovirus, an HIV virus, a herpesvirus, or the like. The gene vector can be obtained by inserting a gene for transfer into a virus vector directly according to a conventional method, for example, described in the above references.

A liposome vector may be any vector that can be used as an ordinary liposome vector in gene therapy and includes, for example, a liposome vector obtained by mixing DOTMA, DOPE, DOGS, etc. When a cationic liposome vector is used, transfer efficiency into cells is high. Examples of the fusogenic liposome vector in which a virus and a liposome are fused include a fusogenic liposome vector in which a Sendai virus (HVJ: hemagglutinating virus of Japan) and a liposome are fused, and the like. A gene vector can be obtained by enclosing a gene for transfer into a liposome vector or a fusogenic liposome vector according to a conventional method, for example, described in the above references. The enclosed gene may be in any form that can express the gene in living body and is preferably a form stable in a living body such as a plasmid, etc.

A gene itself can be retained in a gene preparation of the present invention without being inserted into "a vector for gene insertion" which transfers a gene into cells. In this case, a form of a gene may be any form that can express the gene in living body. For example, a gene maybe inserted into what is called an expression vector and the like. A form of a gene is preferably a form stable in a living body such as a plasmid, etc.

"A gene" for transfer may be any gene that can be used in gene therapy and includes, for example, an adenosine deaminase gene, a GM-CSF gene, a thymidine kinase gene, or the like.

"Biocompatible material" is preferably the material which has high biocompatibility and can retain a gene vector or a gene stably in living body. Examples of the biocompatible material include collagen, gelatin, fibrin, albumin, hyaluronic acid, heparin, chondroitin sulfate, chitin, chitosan, alginic acid, pectin, agarose, hydroxyapatite, polypropylene, polyethylene, polydimethylsiloxane, polymer or copolymer of glycolic acid, lactic acid or amino acid, a mixture of two or more kinds of the biocompatible materials above, and the like. A particularly preferred biocompatible material is collagen. It is also preferred to mix collagen with other biocompatible material described in the above. Collagen may be any collagen and includes, for example, collagen soluble in acid, collagen solubilized by an enzyme (for example, atelocollagen, etc.), collagen solubilized by alkali, collagen having modified amino acid side chains, bridged collagen, collagen produced by genetic engineering, or the like. Collagen having modified amino acid side chains includes, for example, succinyl or methyl collagen, or the like. Bridged collagen includes, for example, collagen treated with glutaraldehyde, hexamethylenediisocyanate or a polyepoxy compound, or the like (Fragrance J., 1989-12, 104–109, Japanese Patent KOKOKU (examined) No. 7 (1995)-59522)).

"An additive" may be added to a preparation of the present invention according to necessity in order to stabilize a gene vector and the like, accelerate gene transfer into cells or nuclei or regulate the release of a gene vector and the like. An additive may be any additive that can achieve the purpose and includes, for example, sucrose, glycine, chondroitin sulfate, gelatin, albumin, cytokine, a mixture of the High Mobility Group Proteins HGM-1 and HGM-2 (High Mobility Group-1, -2 Mixture; Experimental Medicine, 12, 184 (1994), BIOTHERAPY, 8, 1265 (1994)), chloroquine, polylysine (Hepatology, 22, 847 (1995)), Transfectam (Trademark, Wako Pure Chemical Industries, Ltd.), or the like.

In the case wherein collagen is mixed with another biocompatible material or an additive, the content of collagen may be at least 10 w/w %, preferably at least 30 w/w %, more preferably at least 50 w/w %, and most preferably at least 70 w/w %.

The content of biocompatible material in the gene preparation is varied depending on size, kind and the like of the gene vector or the gene and kind and the like of the biocompatible material.

A preferred content of biocompatible material in a gene preparation is 0.01–30 w/w % under the condition that the gene preparation is in a living body, more preferably 0.05–10 w/w %, and most preferably 0.05–5 w/w %.

Furthermore, the content of biocompatible material in the gene preparation is varied depending on the particular preparation. For example, in the case wherein collagen is used as the biocompatible material, the preferred range of the content will be described below.

When the preparation is in gel form, a preferred content of collagen is 0.01–25 w/w %, more preferably 0.05–10 w/w %, most preferably 0.05–5 w/w %. However, when the content of collagen is 2% or more, it is preferred that an additive is added at 5–900 w/w % of collagen.

When the preparation is in film form, a preferred content of collagen is 0.2–30 w/w % as a content before drying, more preferably 0.3–5 w/w %, most preferably 0.4–2 w/w %. However, when a content of collagen is 1% or more, it is preferred that an additive is added at 5–900 w/w % of collagen.

When the preparation is in a solid rod form, the preferred content of collagen is 10–30 w/w % as a content before drying and it is preferred that an additive is added at 5–100 w/w % of collagen.

A gene preparation of the present invention is not limited to a specific form. The preparation can be in solution, suspension, water-containing gel, film or sponge. Solid forms can be shaped as a rod, sphere and the like. However, a preferred form is generally a solution, suspension or water-containing gel, though the form of the preparation is varied depending on kind, size and the like of a vector for gene insertion.

A gene preparation is obtained by keeping a content of biocompatible material in the gene preparation within the above preferred range under the condition that the gene preparation is in a living body.

Examples of methods for producing a gene preparation in a form of solution, suspension or water-containing gel include (1) a method which comprises mixing a powder, solution, suspension or gel of a gene vector or a gene (referred to as a gene vector and the like below) with a carrier in a form of a solution or gel to which an additive is added according to necessity, (2) a method which comprises making a solution, suspension or gel of a gene vector and the like penetrate into a carrier that is in powder form to which an additive is added according to necessity, or (3) a method which comprises making a solution, suspension or gel of a gene vector and the like penetrate into a carrier that is a sponge to which an additive is added according to necessity and kneading them together. The methods for making a gene preparation of the present invention are not limited to such methods.

Examples of methods for producing a gene preparation in a solid form include (1) a method which comprises mixing a powder, solution, suspension or gel of a gene vector and the like with a carrier in a form of solution or gel to which an additive is added according to necessity and drying the mixture, (2) a method which comprises mixing a powder, solution, suspension or gel of a gene vector and the like with a carrier in powder form to which an additive is added according to necessity and drying the mixture, (3) a method which comprises making a solution, suspension or gel of a gene vector and the like penetrate into a carrier in the form of a sponge to which an additive is added according to necessity and drying the sponge, (4) a method which comprises making a solution, suspension or gel of a gene vector and the like penetrate into a carrier in the form of a sponge to which an additive is added according to necessity and drying the sponge as it stands or kneading and drying the sponge after adding water and the like according to necessity, (5) a method which comprises crushing and press-molding a solid product obtained by a method according to (1) to (4), or (6) a method which comprises mixing a powder of a gene vector and the like with a carrier that is a powder to which an additive is added according to necessity and press-molding the mixture. The present invention is not limited to such methods. The drying method; temperature and moisture at drying; mixing method; temperature and moisture at mixing; method for press-molding; temperature, moisture and compressing pressure at press-molding; solution velocity of carrier solution and gene vector solution; and solution velocity of mixture of carrier and gene vector solution; and pH may be as same as those in conventional methods.

A gene preparation of the present invention can be administered by various methods according to the disease being treated, the targeted organ and the like. For example, a gene preparation of the present invention can be administered subcutaneously or intramuscularly, or can be administered directly to targeted sites of disease such as kidney, liver, lung, brain and the like. Direct administration to disease site enables organ-selective therapy.

According to the present invention, when a biodegradable material is used as the biocompatible material, it is not necessary to take the biocompatible material out of the body after administration. Furthermore, repeated administrations are possible.

On the other hand, when discontinuance of gene transfer is required depending on the kind or condition of a disease, a gene preparation can be taken out as it stands, and gene transfer can be stopped. For example, if a gene preparation is a solid, it can be taken away by surgery or the like. When gene therapy is conducted by using a gene preparation wherein a gene vector and the like is retained in a vessel or the like having pores through which a virus can pass freely, the vessel or the like can be taken away at termination of the treatment. For example, gene therapy can be conducted by using a vessel (tube) as described in Japanese patent application No. 3 (1991)-120115 (International publication number WO92/20400).

A gene preparation of the present invention can gradually release a gene vector and the like and simultaneously can retain a gene-inserted vector and the like stably in a living body during the sustained release. Therefore, the time of effective gene expression after a single administration can be extended by controlling the period of gene transfer into cells by delaying contact between cells and vectors.

A gene preparation of the present invention also provides for a high frequency of transformation. That is, the proportion of cells in a culture or tissue contacted with a gene preparation of the invention that take up the nucleic acid and are thus transformed is very high.

A gene preparation of the present invention also enables repeated administrations of a gene vector such as a virus vector and the like which is otherwise difficult to administer repeatedly due to appearance of neutralizing antibodies in a subject.

Furthermore, a gene preparation of the present invention enables regulation of gene expression because the gene preparation can be taken away when termination of treatment is intended.

EXAMPLES

Example 1

A gene preparation was prepared by mixing 0.9 ml of culture medium containing $10^9$ pfu (plaque forming unit) of an adenovirus (Adex1 HST-1; Proc. Natl. Acad. Sci. USA, Vol. 91, 12368 (1994)) inserted with a gene encoding fibroblast cell growth factor HST-1 (FGF4) (prepared according to the method described in Proc. Natl. Acad. Sci. USA, 84, 2980–2984 (1987)) with 0.1 ml of neutral solution of atelocollagen (atelocollagen implant produced by KOKEN: 2% atelocollagen solution). The above adenovirus (Adex1 HST-1) can be obtained by deleting part of E1A, E1B and E3 of adenovirus type 5 (ATCC catalog No. VR-5) according to a method described in J. Virol., 54, 711–719 (1985) or Proc. Natl. Acad. Sci. USA, 93, 1320 (1996) and Cell, 13, 181–188 (1978); inserting a gene of fibroblast cell growth factor HST-1 into the non-proliferative-type adenovirus gene.

Example 2

A gene preparation in gel form is prepared by mixing 0.1 ml of 2% atelocollagen neutral solution with 0.9 ml of culture medium containing $10^9$ pfu of Adex1 HST-1 and then keeping the mixture at 37° C.

Example 3

A gene preparation is prepared by obtaining a sponge by lyophilizing atelocollagen neutral solution; cutting the sponge about 5 mm of square; adding the cut sponge to 1 ml of culture medium containing $10^9$ pfu of Adex1 HST-1; and letting the sponge stand overnight.

Example 4

A gene preparation is prepared by lyophilizing a gene preparation in gel form that is prepared in Example 2.

Example 5

A gene preparation in pellet form (a compressed product in the shape of a rod) is prepared by again lyophilizing the gene preparation that is obtained in Example 3 and compressing the lyophilized sponge into a rod shape.

Example 6

A gene preparation is prepared by mixing a plasmid vector which is obtained by inserting fibroblast cell growth factor HST-1 (FGF4) into an expression vector (pRc/CMV) having a cytomegalovirus (CMV) promoter with a liposome (DMRIE-C (produced by GIBCO-BRL)) and then mixing a solution containing the liposome with the same volume of atelocollagen neutral solution.

Example 7

A gene preparation in bead form is prepared by mixing 1 ml of culture medium containing $10^9$ pfu of Adex1 HST-1 with 1 ml of 1% alginic acid solution; adding the alginic acid solution containing the vector drop by drop to 0.5% calcium chloride solution through a nozzle to obtain beads of 1 mm diameter; and collecting the beads by centrifugation.

Example 8

A gene preparation in bead form is prepared by mixing 1 ml of culture medium which contains $10^9$ pfu of Adex1 HST-1 with 1 ml of 5% agarose gel solution warmed to 45° C.; adding the mixed solution drop by drop to a phosphate buffered saline solution at 10° C. through a nozzle to obtain beads of 1 mm diameter; and collecting the beads by centrifugation.

Example 9

A gene preparation is prepared by enclosing the gene preparation which was obtained in Example 1 in a bag made of polyester (made from artificial blood vessel) (Micron (trademark, produced by INTERVASCULAR).

Example 10

As same as Example 1, 1 ml of a gene preparation was prepared by mixing culture medium containing $10^9$ pfu of Adex1 HST-1 with atelocollagen neutral solution so as to come to be 0.1, 0.2, 0.4, 1.0 or 2.0 w/w % in final concentration of atelocollagen.

Example 11

A gene preparation in gel form is prepared by mixing 5 ml of aqueous solution which contains a plasmid pOG44 (purchased from Stratagene) at a concentration of 73.25 µg/ml with 5 g of atelocollagen acid solution (containing 2% atelocollagen, pH 3.5); lyophilizing the mixture to obtain a sponge; adding distilled water to the sponge so as to come be 0.4, 2, 5, 10 or 20 w/w % in a concentration of atelocollagen.

Example 12

A gene preparation in gel form is prepared by mixing 5 ml of aqueous solution which contains a plasmid pOG44 at a concentration of 73.25 µg/ml with 5 g or 2.5 g of atelocollagen acid solution; adding 260 µl or 640 µl of aqueous solution of human serum albumin (80 mg/ml) to the mixture and mixing them; lyophilizing the mixture to obtain a sponge; adding distilled water to the sponge so as to come be 10 w/w % in the total concentration of atelocollagen and human serum albumin.

Example 13

A gene preparation in a form of film is prepared by spreading and gradually drying the gene preparation in gel form that is obtained in Example 11 on a glass.

Example 14

A gene preparation in rod form is prepared by squeeze-molding and gradually drying the gene preparation in gel form that is obtained in Example 11 or 12.

Comparative Example 1

Figure 1:
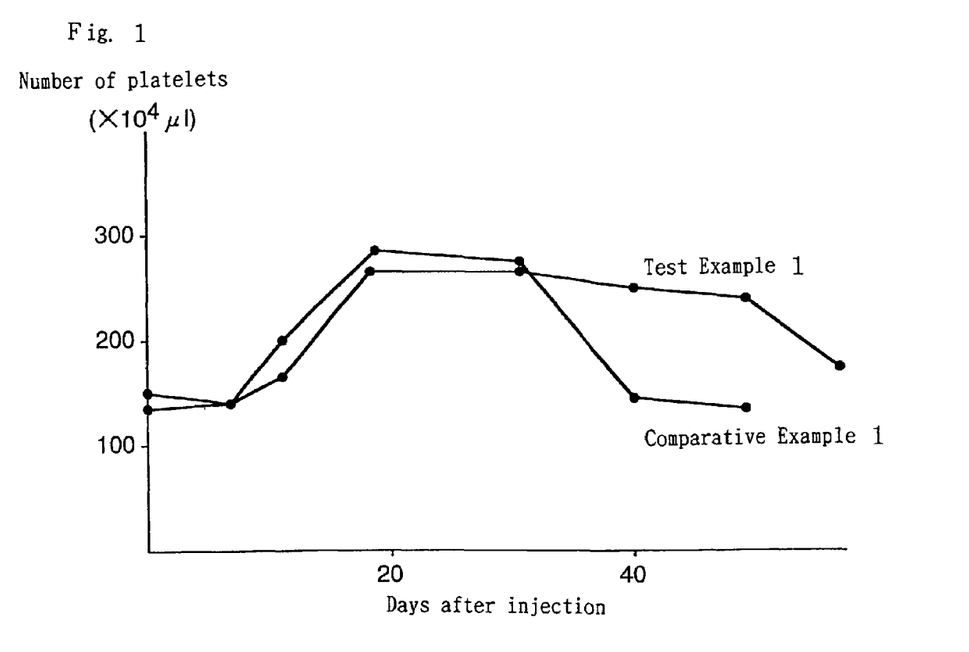
FIG. 1 is a graph showing a time course of the number of platelets in Test Example 1 and Comparative Example 1.
Figure 2:
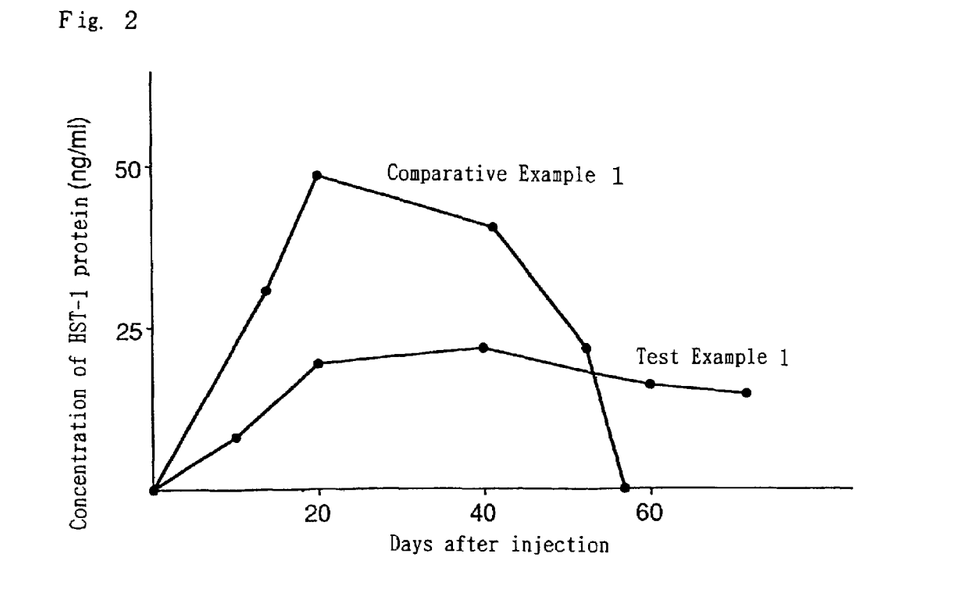
FIG. 2 is a graph showing a time course of HST-1 in peripheral blood in Test Example 1 and Comparative Example 1.

One ml of culture medium containing $10^9$ pfu of Adex HST-1 was administered intraperitoneally to a mouse. Then, on about the 12th day after administration, the number of platelets increased approximately two-fold, and this effect lasted to the 20–30th day. Furthermore, the concentration of HST-1 in peripheral blood was 50 ng/ml and at its maximum on the 20th day after administration. However, the concentration of HST-1 could not be maintained at a fixed level differently from the preparation of Example 1 below and HST-1 could not be detected in blood on the 60th day after administration. These results are shown in FIGS. 1 and 2.

Test Example 1

1.0 ml of a gene preparation which had been prepared in Example 1 was administered intraperitoneally to a mouse. Then, on about the 12th day after administration, the number of platelets increased approximately two-fold, and this effect lasted beyond the 50th day. Furthermore, the concentration of HST-1 in peripheral blood was maintained at 20 ng/ml beyond the 80th day after administration. These results are shown in FIGS. 1 and 2.

Test Example 2

1.0 ml of a gene preparation prepared as in Example 2 is administered intraperitoneally to a mouse. Then, on about the 12th day after administration, the number of platelets increases approximately two-fold, and this effect lasts beyond the 60th day after administration.

Test Example 3

A gene preparation prepared as in Example 3 is administered intraperitoneally to a mouse. Then, on about the 12th day after administration, the number of platelets increases approximately two-fold, and this effect lasts beyond the 60th day after administration.

Test Example 4

Figure 3:
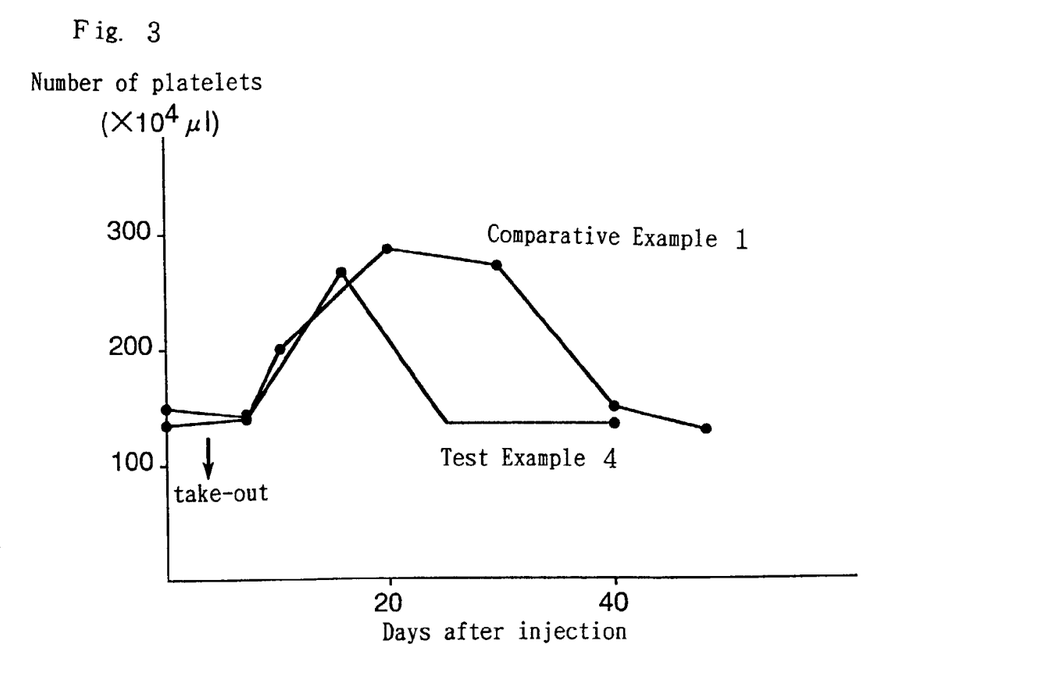
FIG. 3 is a graph showing a time course of the number of platelets in Test Example 4 and Comparative Example 1.

A gene preparation which had been prepared in Example 1 was administered intraperitoneally to a mouse, and the gene preparation was taken out on the third day after administration. As a result, on about the 12th day after administration the number of platelets approximately doubled, then decreased and returned to the normal level on about the 25th day after administration. These results are shown in FIG. 3.

Test Example 5

Figure 4:
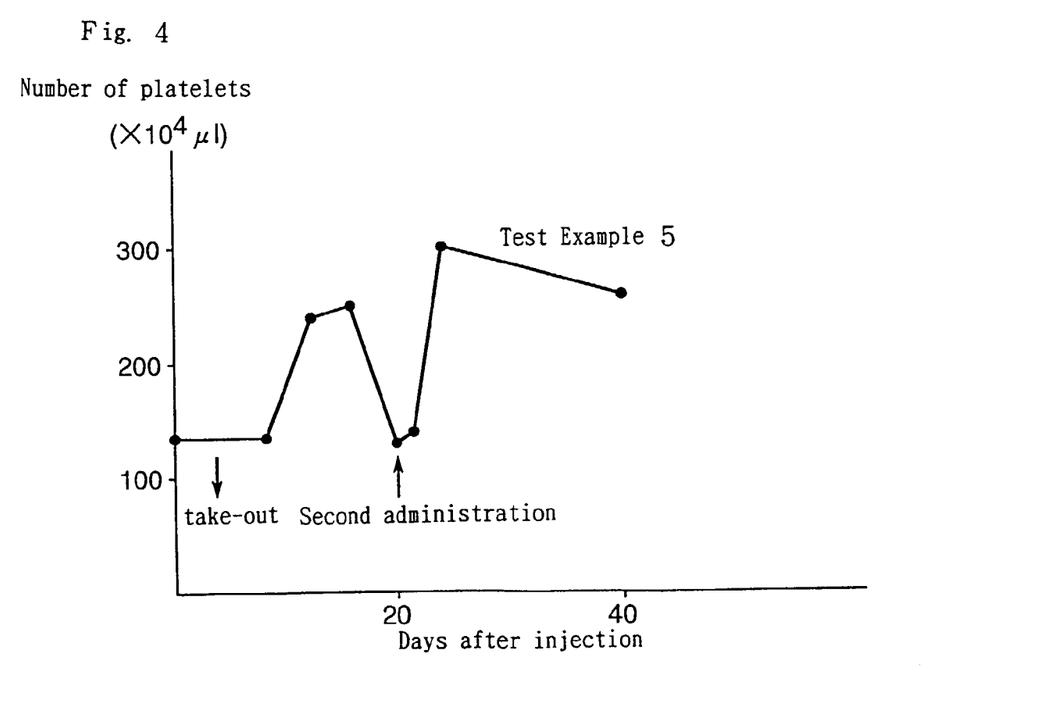
FIG. 4 is a graph showing a time course of the number of platelets in Test Example 5.

A gene preparation which had been prepared in Example 1 was administered intraperitoneally to a mouse and the gene preparation was taken out on the third day after administration. On the 20th day after administration a gene preparation which had been prepared in Example 1 was administered again As a result, on about the 12th day after administration the number of platelets approximately doubled, then decreased and returned to the normal level on about the 20th day after administration. Immediately after the second administration, the number of platelets again increased approximately two-fold, and this effect lasted beyond the 40th day after the first administration. These results are shown in FIG. 4.

Test Example 6

Figure 5:
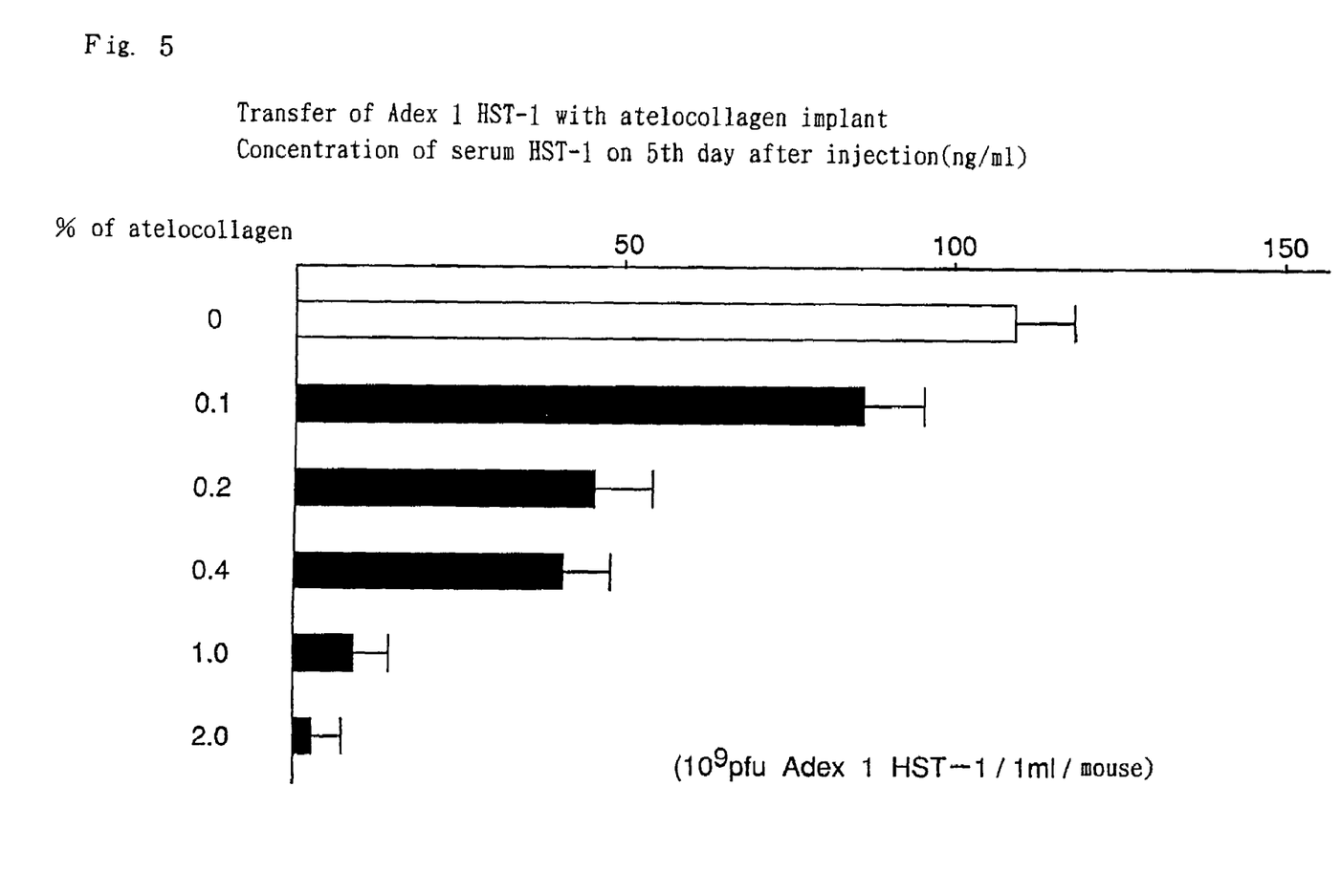
FIG. 5 is a graph showing dose-dependency of collagen on the amount of HST-1 in peripheral blood in Test Example 6.

Each of 5 gene preparations which had been prepared in Example 10 or 1 ml of culture medium which contained $10^9$ pfu of Adex HST-1 and was completely free from collagen was administered intraperitoneally to a mouse. The concentration of HST-1 protein in peripheral blood was determined on the 5th day after administration. The results are shown in FIG. 5. The data show that the serum concentration of HST-1 protein deceased with increasing concentration of collagen in the preparation.

Test Example 7

Figure 6:
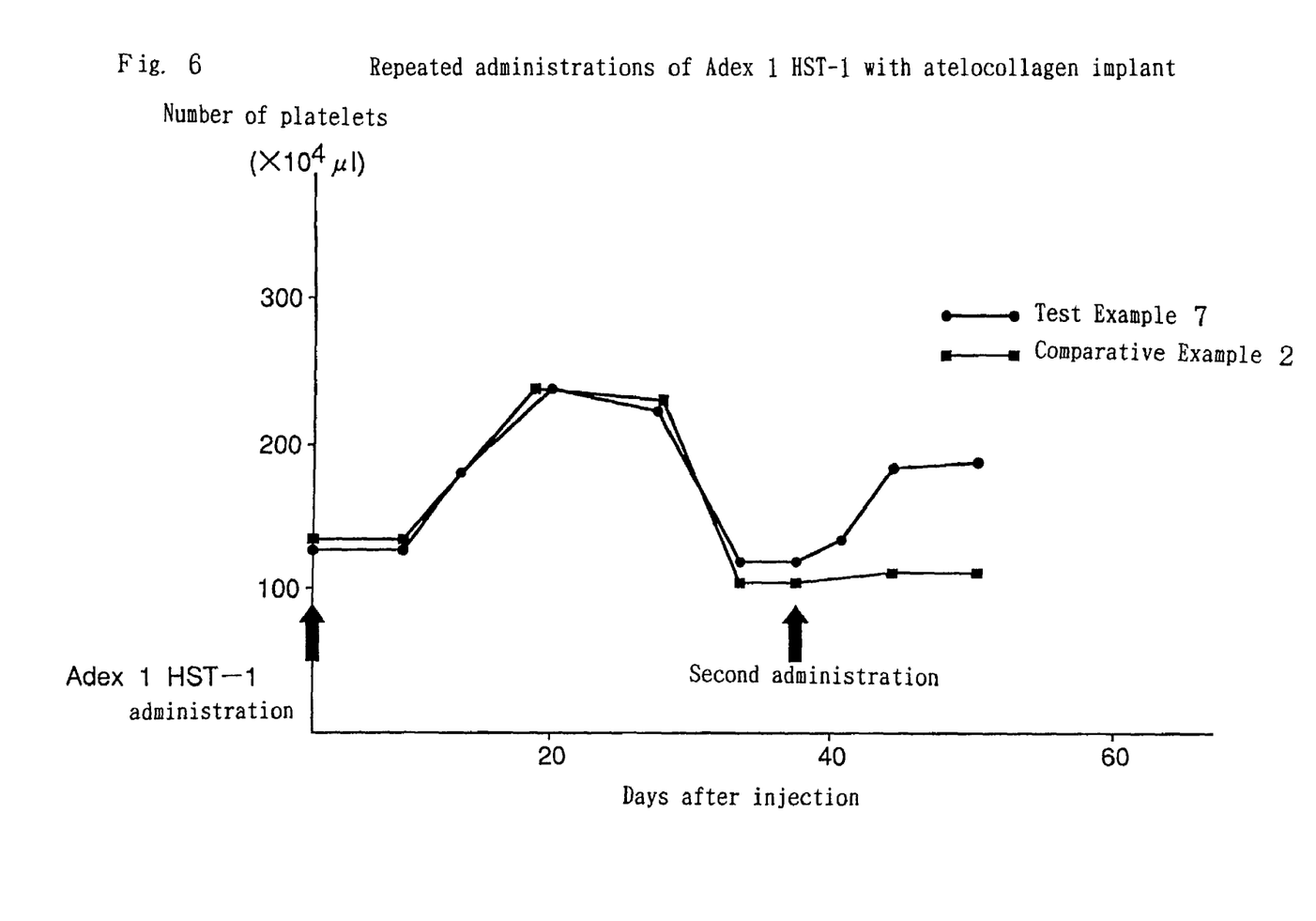
FIG. 6 is a graph showing a time course of the number of platelets in Test Example 7 and Comparative Example 2.

As a result that 1 ml of culture medium containing $10^9$ pfu of Adex HST-1 was administered intraperitoneally to a mouse, the number of platelets approximately doubled by the 12th day after administration, then decreased and returned to the normal level on about the 35th day after administration. On the 37th day after the first administration, 1 ml of an atelocollagen-containing gene preparation which had been prepared in Example 1 was administered again. Immediately after that, the number of platelets increased approximately two-fold, and this effect lasted throughout the remaining term of the experiment. These results are shown in FIG. 6.

Comparative Example 2

One ml of culture medium containing $10^9$ pfu of Adex HST-1 was administered intraperitoneally to a mouse and again administered on the 37th day after the first administration. As a result, on about the 12th day after the first administration the number of platelets approximately doubled, then decreased and returned to the normal level on about the 35th day after the first administration. Platelets did not increase after the second administration of Adex HST-1. These results are shown in FIG. 6.

The results in Test Example 7 and Comparative Example 2 reveal that it is possible to administer a gene preparation prepared in Example 1 repeatedly in contrast with the result obtained upon repeated administrations of an adenovirus vector not formulated according to the present invention. The inability to make a repeated administration is due to the appearance of neutralizing antibodies.

What is claimed is:

1. A method for delivering a gene for uptake by a cell of a subject, comprising administering subcutaneously, intramuscularly, or intraperitoneally a sustained release gene preparation comprising atelocollagen and an intended gene or a vector comprising said intended gene, wherein said atelocollagen is present in the amount of 0.01–25 w/w % of the preparation, wherein said gene is thereby taken up by said cell of said subject.

2. The method according to claim 1, wherein the atelocollagen is present in the amount of 0.05–10 w/w % of the preparation.

3. The method according to claim 2, wherein the atelocollagen is present in the amount of 0.05–5 w/w % of the preparation.

4. The method according to any one of claims 1–3 wherein the preparation further comprises an additive.

5. The method according to claim 4, wherein the atelocollagen is present in the amount of 2 w/w % or more of the preparation, and the additive is present in the amount of 5–900 w/w % of the atelocollagen.

6. The method according to any one of claims 1–3, wherein the preparation is in a gel form.

7. A method for delivering a gene for uptake by a cell of a subject, comprising administering subcutaneously, intramuscularly, or intraperitoneally a controlled release gene preparation comprising atelocollagen, an additive and an intended gene or a vector comprising said intended gene, wherein said atelocollagen is present in an amount of 0.01–25 w/w % of the preparation, wherein said gene is thereby taken up by said cell of said subject.

8. A method for delivering a gene for uptake by a cell of a subject, comprising administering subcutaneously, intramuscularly, or intraperitoneally a sustained release gene preparation obtained by drying a gel comprising 0.2–30 w/w % of atelocollagen, and an intended gene or a vector comprising said intended gene, wherein said gene is thereby taken up by said cell of said subject.

9. The method according to claim 8, wherein the atelocollagen is 0.3–5 w/w % in the gel.

10. The method according to claim 9, wherein the atelocollagen is 0.4–2 w/w % in the gel.

11. The method according to any one of claims 8–10, wherein the gel further comprises an additive.

12. The method according to claim 11, wherein the atelocollagen is 1% or more in the gel, and the additive is 5–900 w/w % of the atelocollagen.

13. The method according to any one of claims 8–10, wherein the preparation is in a form of a film.

14. A method for delivering a gene for uptake by a cell of a subject, comprising administering subcutaneously, intramuscularly, or intraperitoneally a controlled release gene preparation obtained by drying a gel comprising 0.2–30 w/w % of atelocollagen, an additive, and an intended gene or a vector comprising said intended gene, wherein said gene is thereby taken up by said cell of said subject.

15. A method for delivering a gene for uptake by a cell of a subject, comprising administering subcutaneously, intramuscularly, or intraperitoneally a sustained release gene preparation obtained by drying a gel comprising 10–30 w/w % of atelocollagen, and an intended gene or a vector comprising said intended gene, wherein said gene is thereby taken up by said cell of said subject.

16. The method according to claim 15, wherein the gel further comprises an additive.

17. The method according to claim 16, wherein the additive is present in the amount of 5–100 w/w % of the atelocollagen.

18. The method according to any one of claims 15–17, wherein the preparation is in a rod form.

19. A method for delivering a gene for uptake by a cell of a subject, comprising administering to said subject a sustained release gene preparation obtained by the process comprising:
    obtaining a sponge by lyophilizing a gel comprising 0.05 to 5 w/w % of atelocollagen, and an intended gene or a vector comprising said intended gene;
    obtaining a gel in which the concentration of atelocollagen is 10 to 30 w/w % by adding distilled water to the sponge;
    forming a rod by squeeze molding the gel; and
    drying,
    wherein the gene preparation is administered subcutaneously, intramuscularly, or intraperitoneally.

* * * * *